United States Patent [19]

Takahashi

[11] Patent Number: 4,751,986
[45] Date of Patent: Jun. 21, 1988

[54] ROTOR ROTATING ANGLE LIMITER
[75] Inventor: Ryo Takahashi, Tokyo, Japan
[73] Assignee: Yokogawa Medical Systems, Limited, Tokyo, Japan
[21] Appl. No.: 878,847
[22] PCT Filed: Oct. 17, 1985
[86] PCT No.: PCT/JP85/00583
 § 371 Date: Jun. 26, 1986
 § 102(e) Date: Jun. 26, 1986
[87] PCT Pub. No.: WO86/02251
 PCT Pub. Date: Apr. 24, 1986
[30] Foreign Application Priority Data
 Oct. 18, 1984 [JP] Japan .................. 59-219244
[51] Int. Cl.[4] .............................. F16D 63/00
[52] U.S. Cl. ...................... 188/85; 188/67; 188/82.2
[58] Field of Search .............. 188/85, 80, 82.1, 82.2, 188/82.5, 67

[56] References Cited
U.S. PATENT DOCUMENTS

| 1,950,446 | 3/1934 | Eckroad | 188/80 |
| 2,502,780 | 4/1950 | Dreffein | 188/67 |
| 2,744,416 | 5/1956 | Feigin | 188/85 |
| 2,876,868 | 3/1959 | Nerwin, Jr. | 188/85 |
| 3,055,235 | 9/1962 | Turley | 188/85 |
| 3,094,883 | 6/1963 | Junge et al. | 188/67 |
| 3,554,337 | 1/1971 | Denkowski | 188/82.1 |
| 4,187,429 | 2/1980 | Tomita et al. | |

FOREIGN PATENT DOCUMENTS 53-114978 9/1978 Japan .
55-55638 4/1980 Japan .
56-23508 3/1981 Japan .

Primary Examiner—Randolph A. Reese
Assistant Examiner—Anthony Knight
Attorney, Agent, or Firm—Moonray Kojima

[57] ABSTRACT

A rotor rotating angle limiter in this invention which can set the rotating angle of a rotor to more than one revolution but to less than two revolutions, and is simple in construction and highly reliable, a feature of which is that it consists of rotor (1) whose circumference is circular, stator (3) having a concentric circular arc circumference facing said rotor with a gap between them, a projection having a shorter length than the gap and also installed on the circumference of the rotor facing the stator, two projections installed on the circumference of the stator facing the rotor, having a shorter length than the gap and arranged apart along the circumference of the stator circular arc outside of the orbit of the projection on the rotor, and a rolling element which is inserted between the two projections on the stator and into the gap so that it can cross the orbit of the projection on the rotor and is also movable along the gap.

9 Claims, 2 Drawing Sheets

ROTOR ROTATING ANGLE LIMITER

TECHNICAL FIELD

This invention relates to a rotary angle limiter to restrict the rotating angle of a rotor to more than one revolution but less than two revolutions.

BACKGROUND ART

For a mechanism which stops a rotor at a specified position exceeding one revolution with respect to a body under diagnosis such as a gantry used in an X-ray CT, a stopper becomes necessary to avoid overrunning. One type of conventional stopper consists of a stopper mounting shaft which is installed on the same axis as the rotor rotating shaft and coupled to a drive motor via reduction gears and as a result rotates less than one revolution, a stopper which is installed on this stopper mounting shaft and a stopper contact member on a rotor, wherein when the rotor rotates in the direction away from the stopper, the stopper rotates in the same direction as the rotor but at a slower speed than the rotor and the stopper contact member on the rotor after having turned one revolution clashes against the stopper, thereby stopping the rotor. Another type of conventional stopper consists of a cam which is coupled to a motor to rotate a rotor via reduction gears and a limit switch which is actuated by this cam, wherein when the rotor rotates at an angle exceeding a specified range, the power supplied to the motor is turned off by actuating the limit switch, causing the rotor to stop with the brakes on. The disadvantage of these conventional stoppers is that they require reduction gears, which increases cost and reduces reliability.

DISCLOSURE OF INVENTION

The purpose of the present invention is to provide a rotor rotating angle limiter which is less expensive and more reliable than conventional models.

A feature is that it consists of a rotor whose circumference is circular, a stator having a concentric circular arc circumference facing said rotor with a gap between them. A projection having a shorter length than the gap is installed on the circumference of the rotor facing the stator, and two projections are installed on the circumference of the stator facing the rotor, having a shorter length than the gap and arranged apart along the circumference of the stator circular arc outside of the orbit of the projection on the rotor. A rolling element is inserted between the two projections on the stator and in the gap so that it can cross the orbit of the projection on the rotor and is also movable along the gap.

BREIF DESCRIPTION OF DRAWINGS

FIG. 1 illustrates a simplified configuration of one embodiment in this invention.

FIGS. 2a–d illustrate operating diagrams of the above embodiment in this invention.

BEST MODE FOR CARRYING OUT THE INVENTION

Figure 1:
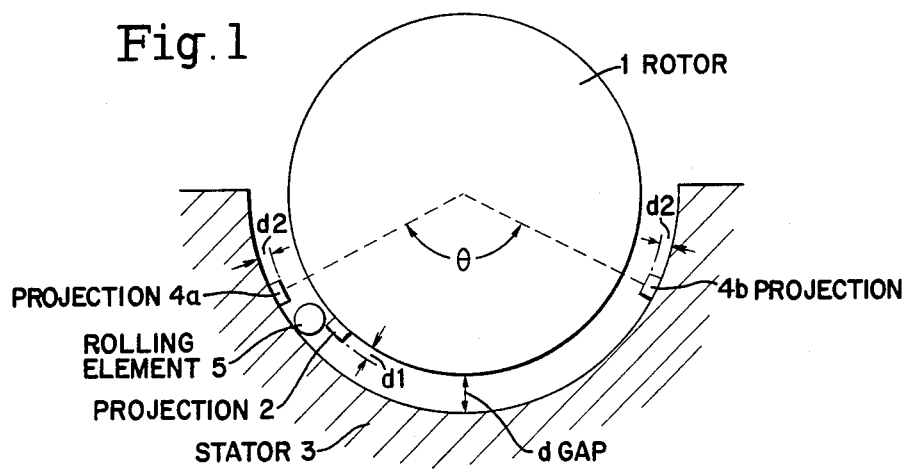
Figure 2A:
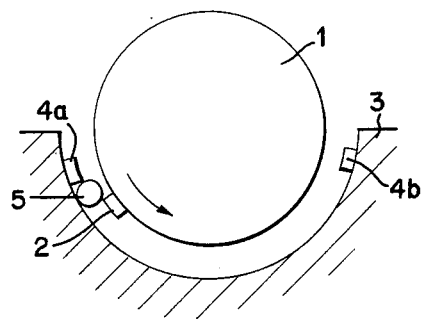
Figure 2B:
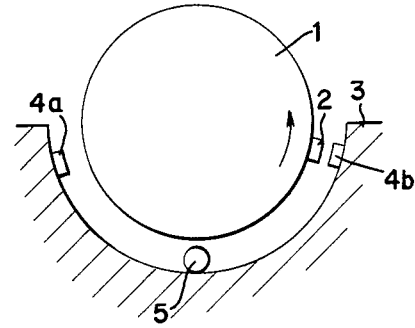
Figure 2C:
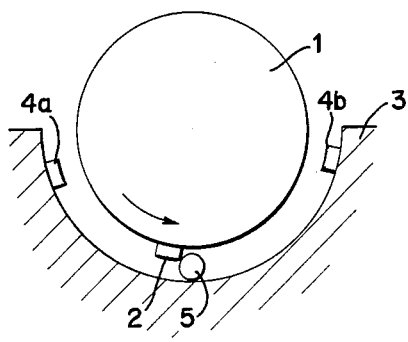
Figure 2D:
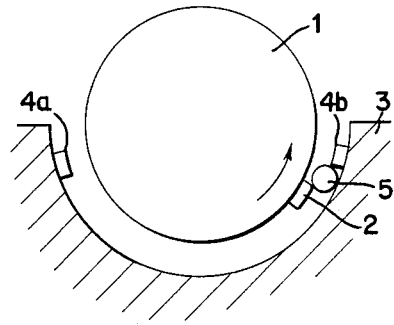

FIG. 1 is a simplified configuration diagram of an embodiment of this invention. In FIG. 1, 1 is a rotor which is supported by an unillustrated support so as to be freely rotatable. If this rotor, for example, is a gantry rotor used in an X-ray CT, it is loaded by an X-ray tube and a radiation detector. 2 is the first projection installed on the circumference of rotor 1 and only one projection exists throughout the whole circumference. 3 is a stator having a circular arc facing the circumference of rotor 1 at a distance of d. 4a and 4b are the two projections installed on the circular arc of stator 3 at a specified angle of $\theta$ and are so shaped and sized that they do not touch projection 2 when rotor 1 rotates through one revolution. In such a dimensional example, FIG. 1 is a case where the relationship of $d_2 < d - d_1$ is established assuming that the height of projections 4a and 4b is $d_2$, the height of projection 2 is $d_1$ and the gap is d. 5 is a rolling element which can be a ball or cylinder whose outer diameter D is slightly smaller than gap d and is placed so as to be movable along gap d between the circumference of rotor 1 and the circular arc of stator 3. Outer diameter D of the rolling element is larger than the distance from the circumference of rotor 1 to the ends of projections 4a and 4b and that from the circular arc of stator 3 to the end of projection 2, i.e. $D > d - d_2$ and $D > d - d_1$. The operation of said device so constructed is described in the following with reference to FIG. 2. Assuming that rotor 1 is now at the position shown in (a), projection 2 contacts projection 4a with the rolling element sandwiched between them so that rotor 1 cannot rotate any more in the clockwise direction. In this state, if rotor 1 rotates in the counterclockwise direction (shown by arrow CCW), rolling element 5 moves down to the bottom of the circular arc of stator 3 as shown in (b), but projection 2 on rotor 1 continues rotating by passing right above projection 4b on stator 3, while projection 2 on rotor 1 rotates by passing right above projection 4a and touches rolling element 5 shown in (c). Further, if rotor 1 rotates in the counterclockwise direction, projection 2 rotates, pushing rolling member 5 up against projection 4b and sandwiching said rolling member between them as shown in (d), thereby stopping rotor 1, since said rotor cannot rotate any more.

In this state, if rotor 1 rotates in the clockwise direction, said rotor returns back to the position shown in (a) by tracing the reverse path.

Through the above operation, rotor 1 can be securely stopped at the specified position after its rotation of more than one revolution but less than two revolutions.

Figure 3:
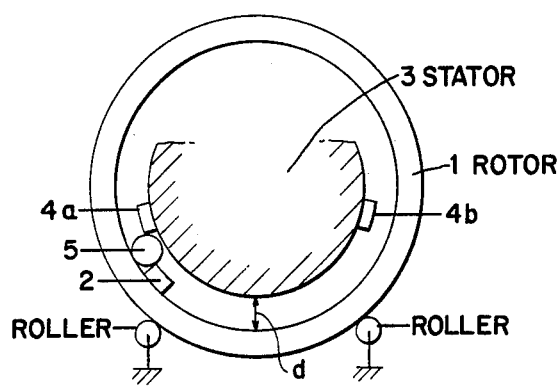
FIG. 3 illustrates a simplified configuration diagram of another embodiment in this invention.

FIG. 3 illustrates a simplified configuration diagram of another embodiment in this invention. In this embodiment, rotor 1 is located outside of stator 3.

Figure 4:
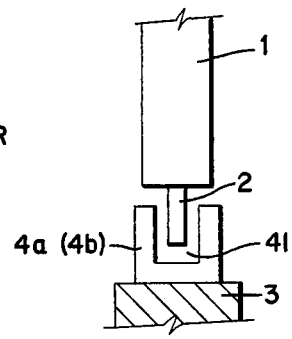
FIG. 4 illustrates a partially modified configuration diagram of the embodiment in this invention.

FIG. 4 is a configuration diagram of another embodiment with projection 2 installed on rotor 1 and projection 4a (4b) installed on stator 3 similar to the embodiment illustrated in FIG. 1. In this embodiment, groove 41 is so formed in projection 4a (4b) that projection 2 on rotor 1 passes through groove 41 without making contact. In this case, groove 41 may be more than one and projection 2 may be more than one so as to correspond to each groove. In addition, the locations of projection(s) 2 and projection(s) 4a (4b) may replace each other.

Figure 5:
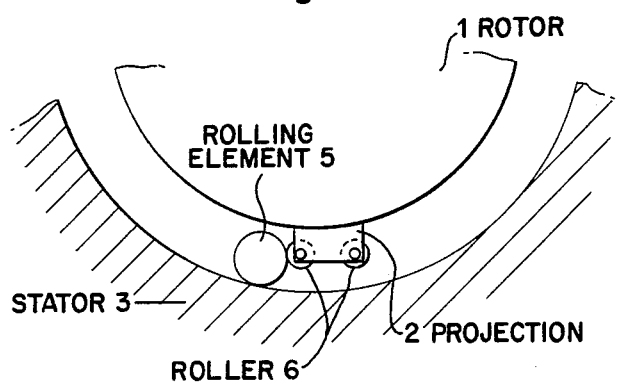
FIGS. 5 and 6 illustrate simplified configuration diagrams of othe embodiment in this invention.
Figure 6:
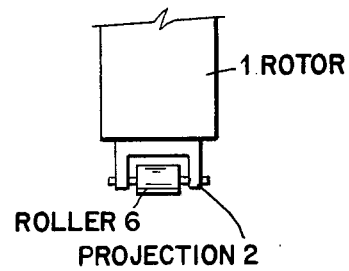

It is desirable that rolling element 5 be made of an elastic material. The use of elastic rolling member 5 is effective for shock absorption when said member contacts said projections. This effect can be further enhanced if projections 4a and 4b are also made of an elastic material. However, it is feared that if rolling element 5 is made of a very soft elastic material, this mechanism may not function normally since rolling element 5 is sandwiched between projection 2 and stator 3. However, sandwiching of rolling member 5 can be prevented if projection 2 is branch-shaped and rollers 6 are shaft-supported between these branches so as to be freely rotatable as shown in FIGS. 5 and 6. As a aforementioned, this invention can result in less expensive and more reliable rotor rotating angle limiters due to the elimination of reduction mechanisms and their extremely simple constructions.

Above is the description of the best form in order to implement this invention. However, a person having ordinary skill in the art to which this invention pertains can also make various modifications within the concept of this invention described in the following claims.

I claim:

1. A rotor rotating angle limiter consisting of a rotor (1) whose circumference is circular, a stator (3) having a concentric circular arc circumference facing said rotor with a gap having a length between them, one projection (2) having a shorter length than the gap length and also installed on the circumference of the rotor facing the stator, two projections (4a and 4b) installed on the circumference of the stator facing the rotor, having a shorter length than the gap length and arranged apart along the circumference of the stator circular arc outside of the orbit of the projection on the rotor, and a circular cylindrical roller (5) inserted within the cylindrical surface created between the rotor and stator and between the two projections on the stator and in the gap so that it can cross the orbit of the projection on the rotor and is also rotatably movable along the gap, wherein a radial space exists between the projection on the rotor and the projections on the stator so that the stator and rotor can rotate with respect to each other unless the roller comes between the projection on the rotor and one of the projections on the stator with the roller being rotated by the relative movement of the rotor and stator until the roller becomes positioned in contact between the projection on the rotor and the one projection on the stator.

2. A rotor rotating angle limiter as claimed in claim 1, wherein:
the sum of the length of the projection installed on the rotor and that of the projections installed on the stator is less than the gap length between the rotor and the stator.

3. A rotor rotating angle limiter as claimed in claim 1, wherein:
the sum of the length of the projection installed on the rotor and that of the projections on the stator is longer than the gap between the rotor and the stator and is shorter than twice the gap, and the projections on the rotor and the stator face each other with either one of their rotating orbits between, and one side of these projections comprises at least two projections located at a distance longer than the thickness of the other in the rotor rotating axis direction.

4. A rotor rotating angle limiter claimed in claim 1, wherein:
the roller is made of an elastic material.

5. A rotor rotating angle limiter claimed in claim 1, wherein:
the projection on the rotor has rollers through which the projection contacts the rolling element.

6. A rotor rotating angle limiter claimed in claim 1 wherein:
at least either one of the projection on the rotor and the projections on the stator is made of an elastic material.

7. A rotor rotating angle limiter claimed in claim 2, wherein at least either one of the projection on the rotor and the projections on the stator is made of an elastic material.

8. A rotor rotating angle limiter claimed in claim 3, wherein at least either one of the projection on the rotor and the projections on the stator is made of an elastic material.

9. A rotor rotating angle limiter claimed in claim 4, wherein at least either one of the projections on the rotor and the projections on the stator is made of an elastic material.

* * * * *